United States Patent
Sieverding

Patent Number: 6,100,261
Date of Patent: Aug. 8, 2000

[54] FUNGICIDAL MIXTURES

[75] Inventor: Ewald Sieverding, St. Johann, Germany

[73] Assignee: American Cyanamid Company, Madison, N.J.

[21] Appl. No.: 09/301,857

[22] Filed: Apr. 29, 1999

Related U.S. Application Data

[60] Provisional application No. 60/085,349, May 13, 1998.

[51] Int. Cl.$^7$ .......................... A01N 43/40; A61K 31/535
[52] U.S. Cl. ........................................ 514/237.5; 514/352
[58] Field of Search ................................. 514/237.5, 352

[56] References Cited

FOREIGN PATENT DOCUMENTS

WO 95/04460  2/1995  Japan .
WO 97/41727  3/1997  WIPO .

OTHER PUBLICATIONS

"The Pesticide Manual", 10$^{th}$ Edition, The British Crop Protection Council and The Royal Society of Chemistry, 1994, pp. 351–352 and 474–5.

*Primary Examiner*—Allen J. Robinson
*Attorney, Agent, or Firm*—Joseph M. Mazzarese

[57] ABSTRACT

A liquid concentrated fungicidal composition containing a fungicidally acceptable carrier and/or surface active agent and synergistically effective amounts of
(a) at least one acrylic acid morpholide of formula I

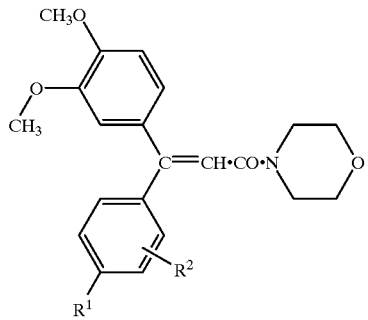

(I)

in which $R^1$ and $R^2$ have the meaning given in claim 1, and
(b) at least one fungicidal N-pyridylaniline compound. This invention also includes a method of controlling the growth of phythopathogenic fungi at a locus which comprises applying synergistically effective amounts of at least one acrylic acid morpholide of formula I and at least one fungicidal N-pyridylaniline compound to the locus.

11 Claims, No Drawings

FUNGICIDAL MIXTURES

This application claims the benefit of U.S. provisional application Ser. No. 60/085,349, filed May 13, 1998.

BACKGROUND OF THE INVENTION

The present invention includes a fungicidal composition comprising a fungicidally acceptable carrier and/or surface active agent and synergistically effective amounts of at least one compound of formula I, and at least one N-pyridylaniline compound.

Fungicidal N-pyridylaniline compounds are known for example from EP 0 031 257. The International patent application WO 95/04460 suggest to prepare fungicidal water dispersible granules containing 3-chloro-N-(3-chloro-5-trifluoromethyl-2-pyridyl)-2,6-dinitro-4-trifluoromethylbenzene and optionally other fungicidal compounds including dimethomorph.

However, until now it has not been known that the compounds of formula I with N-pyridylaniline compounds, when admixed in a tank mix or when co-formulated, would show synergistic effects. Moreover, it has not been known that a liquid concentrated composition comprising a synergistic mixture of these compounds can be advantageously be used for controlling diseases caused by oomycetes, e.g. *Phytophtora infestans*.

A mixture of fungicides shows synergistic effect if the fungicidal activity of the mixture is larger than the sum of activities of the separately applied compounds. The expected fungicidal activity for a given mixture of two fungicides can be calculated as follows (See Colby, S.R., "Calculating synergistic and antagonistic response of herbicide combinations", Weeds 15, pp 20–22 (1967):

$$EE = x + y - x \cdot y/100$$

wherein x is the efficacy in % compared with an untreated control upon treatment with a fungicidal active ingredient A at a dose rate a;

y is the efficacy in % compared with an untreated control upon treatment with a fungicidal active ingredient B at a dose rate b;

EE is the expected efficacy with a combination of fungicidal active ingredients A and B at a dose of a+b, respectively.

If the actual efficacy (E) exceeds the expected (calculated) one (EE), the mixture displays a synergistic effect.

SUMMARY OF THE INVENTION

The present invention includes a liquid concentrated fungicidal composition comprising a fungicidally acceptable carrier and/or surface active agent and synergistically effective amounts of (a) at least one acrylic acid morpholide of formula I

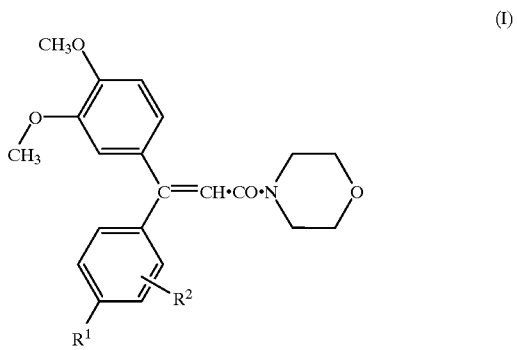

(I)

in which
R$^1$ and R$^2$ each independently represent hydrogen or halogen atom or an optionally substituted alkyl, alkoxy, alkenyl, alkynyl, alkadienyl, aryl, aryloxy, heteroaryl, cycloalkyl, cycloalkenyl, bicycloalkyl or heterocyclyl group, (b) and at least one fungicidal N-pyridylaniline compound.

The fungicidal compounds of formula I to be used according to the present invention are known from European patent application EP 0 120 321.

The present invention also includes a method for controlling the growth of phythopathogenic fungi comprising application of synergistically effective amounts of at least one compound of formula I and at least one N-pyridylaniline compound as defined above.

DETAILED DESCRIPTION OF THE PREFERRED EMBODIMENTS

Surprisingly, a strong synergy between the compounds of formula I and N-pyridylaniline compounds was found when these two compounds were tank mixed or co-formulated, compared to the activity of each compound in a solo formulation.

In general terms, unless otherwise stated, as used herein the term halogen atom may denote a bromine, iodine, chlorine or fluorine atom, and is especially a bromine, chlorine or fluorine atom, in particular a bromine or chlorine atom.

Optionally substituted moieties may be unsubstituted or have from one up to the maximal possible number of substituents. Typically, 0 to 2 substituents are present. Each optionally substituted group independently may be substituted by one or more halogen atoms or nitro, cyano, cycloalkyl, preferably C$_{3-6}$ cycloalkyl, cycloalkenyl, preferably C$_{3-6}$ cycloalkenyl, haloalkyl, preferably C$_{1-6}$ haloalkyl, halocycloalkyl, preferably C$_{3-6}$ halocycloalkyl, alkoxy, preferably C$_{1-6}$ alkoxy, haloalkoxy, preferably C$_{1-6}$ haloalkoxy, phenyl, halo- or dihalo-phenyl or pyridyl groups.

Unless otherwise stated herein, the terms alkyl, alkenyl, alkynyl, alkadienyl and alkoxy as used herein with respect to a radical or moiety refer to a straight or branched chain radical or moiety. As a rule, such radicals have up to 10, in particular up to 6 carbon atoms. Suitably an alkyl or alkoxy moiety has from 1 to 6 carbon atoms, preferably from 1 to 5 carbon atoms. A preferred alkyl moiety is the methyl, ethyl, n-propyl, isopropyl or n-butyl group.

Unless otherwise stated herein, the term aryl, as used herein with respect to a radical or moiety refers to an aryl group having 6, 10 or 14 carbon atoms, preferably 6 or 10 carbon atoms, in particular phenyl being optionally substituted by one or more halogen atoms, nitro, cyano, alkyl, preferably $C_{1-6}$ alkyl, alkoxy, preferably $C_{1-6}$ alkoxy, haloalkyl, preferably $C_{1-6}$ haloalkyl, haloalkoxy, preferably $C_{1-6}$ haloalkoxy groups.

Unless otherwise stated herein, the term cycloalkyl or cycloalkenyl, as used herein with respect to a radical or moiety refers to a cycloalkyl group having 3 to 8 carbon atoms or a cycloalkenyl group having 5 to 8 carbon atoms, preferably 5 to 7 carbon atoms, in particular cyclopentyl, cyclohexyl or cyclohexenyl being optionally substituted by one or more halogen atoms, nitro, cyano, alkyl, preferably $C_{1-6}$ alkyl, alkoxy, preferably $C_{1-6}$ alkoxy.

Unless otherwise stated herein, the term heteroaryl, as used herein with respect to a radical or moiety, refers to an aromatic heterocyclic group having 5 or 6 ring atoms selected from carbon, nitrogen, oxygen and sulfur, at least one of which being nitrogen, oxygen or sulfur being optionally substituted by one or more halogen atoms, nitro, cyano, alkyl, preferably $C_{1-6}$ alkyl, alkoxy, preferably $C_{1-6}$ alkoxy, in particular azolyl, triazolyl, triazoly, furanyl, oxazolyl, thienyl, thiazolyl, dithiazolyl, pyridyl or pyrimidyl.

Unless otherwise stated herein, the term heterocyclyl, as used herein with respect to a radical or moiety, refers to a non-aromatic heterocyclyc group having 5 or 6 ring atoms selected from carbon, nitrogen, oxygen and sulfur, at least one of which being nitrogen, oxygen or sulfur being optionally substituted by one or more halogen atoms, nitro, cyano, alkyl, preferably $C_{1-6}$ alkyl, alkoxy, preferably $C_{1-6}$ alkoxy, in particular tetrahydropyranyl, tetrahydrofuranyl, tetrahydrothienyl, tetrahydropyridyl or tetrahydropyrimidyl.

Preferred compounds of formula I are those in which $R^1$ and $R^2$ are defined as follows:

|    | $R^1$ | $R^2$ |
|----|-------|-------|
| a) | Cl | H |
| b) | Br | H |
| c) | $CF_3$ | H |
| d) | $CF_3O$ | H |
| e) | propyl | H |
| f) | butoxy | H |
| g) | phenyl | H |
| h) | 4-chlorophenoxy | H |
| i) | H | 3-phenoxy |

Particularly preferred compounds of formula I are those wherein $R^1$ represents a halogen atom and $R^2$ represents a hydrogen atom.

A particularly preferred compound of formula I is dimethomorph, which is described in the "The Pesticide Manual", 10th Edition, The British Crop Protection Council and The Royal Society of Chemistry, 1994, (hereinbelow abbreviated as "Pesticide Manual"), page 236.

Preferred N-pyridylaniline compounds are the compounds of formula II,

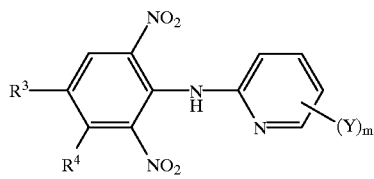

wherein
  $R^3$ and $R^4$ each independently represent a hydrogen or halogen atom or an optionally substituted alkyl group, preferably chloro or trifluoromethyl;
  Y each independently represents a halogen atom or an optionally substituted alkyl group, preferably chloro or trifluoromethyl;
  m is 0 or an integer of 1, 2, 3 or 4, preferably 2.
The following compounds of formula II are preferred:

|    | $R^3$ | $R^4$ | $(Y)_m$ |
|----|-------|-------|---------|
| a) | $CF_3$ | Cl | 3-Cl 5-$CF_3$ |
| b) | $CF_3$ | Cl | 3-Cl 5-Cl |
| c) | $CF_3$ | H | 3-Cl 5-$CF_3$ |
| d) | $CF_3$ | H | 3-Cl 5-Cl |
| e) | $CF_3$ | 2-hydroxyphenoxy | 3-Cl 5-$CF_3$ |
| f) | $CF_3$ | ethoxy | 3-Cl 5-$CF_3$ |

A particularly preferred compound of formula II is fluazinam, which is described in the "The Pesticide Manual", page 474.

Preferred fungicidal compositions of this invention include liquid concentrated co-formulations comprising the following constituents:
  a surface active agent;
  an acrylic acid morpholide of formula I, in particular dimethomorph;
  at least one N-pyridylaniline compound; in particular fluazinam,
  optionally a foam breaking agent, in particular a mixture of perfluoroalkyphosphonic acids and/or perfluoro-alkylphosphinic acids, in particular Defoamer® SF or Fluowette® PL, which are commercially available from Clariant GmbH, Germany.

The compounds of formula I and the N-pyridylaniline compound are to be applied together, in synergistically effective amounts. They exhibit an extraordinary efficacy against a broad range of phytopathogenic fungi. They are systemic and may be applied as leaf or soil fungicides.

The mixture according to the invention may be preferably applied for controlling diseases caused by phytopathogenic fungi of the genera of Phythophthora, Plasmopara, Pseudoperonospora, Bremia, Peronospora, Altemaria, Guignardia, Septoria, Botrytis, Phomopsis, Rhizoctonia, and in particular of the species *Phythophthora infestans* and *Plasmopara viticola.*

The preferred application rate of the compound of formula I according to this invention is in the approximate range of 5 to 2000 grams of active ingredient (g a.i.) per hectare, with rates of about 50–500 g a.i./ha often achieving satisfactory control. The optimal rate for a specific application will depend on the crop(s) under cultivation and the predominant species of infesting fungus, and readily may be determined by established biological tests known to those skilled in the art.

In general, the preferred application rate of the N-pyridylaniline compound is in the approximate range of 20 to 500 g a.i./ha, preferably 50–300 g a.i./ha.

The optimal rate for the formula II fungicidal compound will, however, depend on the crop(s) under cultivation and the level of infestation by the fungus, and can readily be determined by established biological tests.

The preferred ratio (by weight) of the compound of formula I to the N-pyridylaniline compound is from 1:20 to 20:1, more preferably from about 1:10 to about 10:1, in particular from about 1:2 to about 2:1.

The active compounds may be formulated together in a suitable ratio according to the present invention, together with carriers and/or additives known in the art.

Accordingly, the invention further provides a concentrated liquid fungicidal composition which comprises a carrier and, as active ingredient, at least one compound of formula I as defined above and a N-pyridylaniline compound, in particular fluazinam.

A method of making such a composition is also provided, which comprises bringing a compound of formula I and a N-pyridylaniline compound into association with at least one carrier. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredients.

A carrier useful in a composition according to the invention may include any material which facilitates application of the composition to the locus to be treated, which locus may, for example, be a plant, seed or soil, or which will facilitate storage, transport or handling. A carrier may be a solid or a liquid, including material which is normally a gas but which has been compressed to form a liquid.

The compositions may be manufactured into, e.g., emulsion concentrates, solutions, oil in water emulsions, suspension concentrates, micro-capsules, gels and other formulation types by well-established procedures. These procedures include intensive mixing and/or milling of the active ingredients with other substances, such as solvents, solid carriers, surface active compounds (surfactants), and optionally solid and/or liquid auxilaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different solvents are often suitable.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants used in formulations of this invention may be nonionic, anionic, cationic or zwitterionic substances with good dispersing, emulsifying and wefting properties depending on the nature of the compound according to general formula I to be formulated, and may also include mixtures of individual surfactants.

The compositions of the invention may, for example, be formulated as solutions, emulsifiable concentrates, emulsions, suspension concentrates and aerosols. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected as disclosed for example by U.S. Pat. No. 5,705,174.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient. Preferably, linoleic acid is used as adjuvant.

As a commodity, the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| active ingredient | dimethomorph/fluazinam (1:1 w/w) | 30% (w/v) |
| emulsifier(s) | Atlox ® 4856 B and Atlox ® 4857 B[1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| solvent | Shellsol ® A[2] (mixture of $C_9$–$C_{10}$ aromatic hydrocarbons) | to 1000 ml |
| Suspension Concentrate (SC) | | |
| active ingredient | dimethomorph/fluazinam (1:1 w/w) | 50% (w/v) |
| dispersing agent | Soprophor ® FL[3] (polyoxyethylene polyaryl phenyl ether phosphate amine salt) | 3% (w/v) |

-continued

| | | |
|---|---|---|
| antifoaming agent | Rhodorsil ® 422[3] (nonionic aqueous emulsion of polydimethylsiloxanes) | 0.2% (w/v) |
| structure agent | Kelzan ® S[4] (Xanthan gum) | 0.2% (w/v) |
| antifreezing agent | Propylene glycol | 5% (w/v) |
| biocidal agent | Proxel ®[5] (aqueous dipropylene glycol solution containing 20% 1,2-benisothiazolin-3-one) | 0.1% (w/v) |
| Water | | to 1000 ml |

[1] Product commercially available from ICI Surfactants
[2] Product commercially available from Deutsche Shell AG
[3] Product commercially available from Rhône-Poulenc
[4] Product commercially available from Kelco Co.
[5] Product commercially available from Zeneca A concentrated composition according to the invention preferably contains from 0.5% to 95% by weight of active ingredients.

In a preferred embodiment, the active ingredients are each added to the tank mix as a solo formulation containing a single active ingredient to form the composition of this invention.

Therefore, the present invention also relates to a kit for the preparation of a spray mixture consisting of two separate units:

(i) a unit which comprises at least one fungicide of formula I, conventional adjuvants and carriers;

(ii) a unit which comprises at least one N-pyridylaniline compound, in particular fluazinam, conventional adjuvants and carriers.

In a preferred embodiment, the said kit will consist of two bottles with dispensing means which allow the easy and correct addition of appropriate amounts of the active ingredients to the tank mix.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The test results described below demonstrate the enhancement in efficacy (synergy) of the combination of the compounds of formula I and N-pyridylaniline compounds of this invention.

EXAMPLE 1

For this greenhouse study, formulated dimethomorph (500 g/l SC,) and commercially available formulated fluazinam (500 g/l SC, trade name SHIRLAN) were used.

Potato var. 'Bintje' were grown up in small pots and, after having obtained a height of approximately 10 cm, were sprayed with 12.5 g ai/ha of dimethomorph or fluazinam using the 'solo' products, and with the combination of 12.5+12.5 g ai/ha of dimethomorph+fluazinam (in-tank mixture). The spray volume was equivalent to 400 l/ha into which the products were suspended. A track sprayer with an even spray nozzle was used for the application. Five days after application of the products the plants were inoculated with a zoospore suspension of Phytophthora infestans. The plants were then transferred to a greenhouse cabine in which the relative humidity was maintained at around 99–100%.

Disease symptoms (potato late blight) were assessed 11 and 15 days after application (DAT) of the products. The efficacy of the products was calculated in relation to the untreated plants. The results of this evaluation are shown in Table I.

TABLE I

| | | 11 days efficacy (%) | | 15 days efficacy (%) | |
|---|---|---|---|---|---|
| Treatment | dose (g/ha) | obtained | expected | obtained | expected |
| dimethomorph | 12.5 | 25 | — | 22 | — |
| fluazinam | 12.5 | 37 | — | 27 | — |
| dimethomorph + fluazinam | 12.5 12.5 | 89 | 53 | 78 | 43 |

Whereas the 'solo' products provided 25 and 22% disease control (dimethomorph) and 37 and 27% disease control (fluazinam) at 11 and 15 DAT, the in-tank mixed combination of dimethomorph with fluazinam provided 89 and 78% disease control at 11 and 15 DAT, respectively. The efficacy of the combination was clearly higher than could have been expected from the additive efficacy of the two products which would have been 53 and 43% at 11 and 15 DAT, respectively. Hence, it is clear that synergism occurred between dimethomorph and fluazinam. When an adjuvant was added to the in-tank mixture of dimethomorph plus fluazinam, the synergism was also observed.

EXAMPLE 2

Effect of fungicidal SC formulations of dimethomorph and fluazinam as active ingredients in combination with an adjuvant against potato late blight. The adjuvant is formulated as described in the following Recipe:

| | |
|---|---|
| Soprophor 796/B[a] (ethoxypropoxylated tristyrylphenol) | 100 g |
| Edenor SB 0.5[b] | to 1000 ml |

[a] commercially available from Rhône-Poulenc
[b] commercially available composition consisting of about 70% by weight of linoleic acid and about 30% by weight of linolenic acid The formulations were applied in a small band on the leaves, 5 days before inoculation. Fungicidal efficacy at 11 days after treatment is shown in table II:

TABLE II

| treatment | dose (g/ha) | efficacy (%) |
|---|---|---|
| dimethomorph + fluazinam | 25 25 | 86 |
| dimethomorph + fluazinam + linoleic acid | 25 25 500 | 94 |
| linoleic acid | 500 | 9 |

The 94% efficacy was higher than that predicted according to the Colby formula (87%).

What is claimed is:

1. A liquid concentrated fungicidal composition comprising a fungicidally acceptable carrier and/or surface active agent and synergistically effective amounts of dimethomorph and fluazinam in an approximate weight ratio of from 1:20 to 20:1.

2. A composition as claimed in claim 1, wherein the ratio by weight of dimethomorph to fluazinam is in the approximate range of from 1:10 to 10:1.

3. A composition as claimed in claim 1, wherein the ratio by weight of dimethomorph to fluazinam is in the approximate range of from 1:2 to 2:1.

4. A method of controlling the growth of phythopathogenic fungi at a locus which comprises applying to the locus synergistically effective amounts of dimethomorph and fluazinam, wherein the application rate of the fluazinam at the locus is in the approximate range of from 5 to 2000 grams per hectare and the approximate weight ratio of dimethomorph to fluazinam is from 1:10 to 10:1.

5. The method as claimed in claim 4, wherein said approximate ratio is from 2:1 to 1:2.

6. A method of controlling the growth of phythopathogenic fungi at a locus which comprises applying a composition as claimed in claim 1 to the locus, wherein the application rate of the fluazinam at the locus is in the approximate range of from 5 to 2000 grams per hectare.

7. A method of controlling the growth of oomycetes at a locus which comprises applying a composition as claimed in claim 1 to the locus, wherein the application rate of the fluazinam at the locus is in the approximate range of from 5 to 2000 grams per hectare.

8. A method for controlling the growth of oomycetes at a locus, which comprises applying synergistically effective amounts of dimethomorph and fluazinam to the locus in an approximate ratio by weight of from 1:2 to 2:1, wherein the application rate of the fluazinam at the locus is in the approximate range of from 5 to 2000 grams per hectare.

9. A method according to claim 8 wherein said ratio is approximately 1:1.

10. A method according to claim 8 further comprising adding a fungicidally enhancing amount of linoleic acid to the locus.

11. A method for controlling the growth of Phytophthora infestens at a locus which comprises applying synergistically effective amounts of dimethomorph and fluazinam to the locus in an approximate weight ratio of from 2:1 to 1:2.

* * * * *